United States Patent
Lal et al.

(10) Patent No.: US 6,958,415 B2
(45) Date of Patent: Oct. 25, 2005

(54) SYNTHESIS OF PENTAFLUOROSULFURANYL ARYLENES

(75) Inventors: Gauri Sankar Lal, Whitehall, PA (US); Kristen Elaine Minnich, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 144 days.

(21) Appl. No.: 10/713,231

(22) Filed: Nov. 14, 2003

(65) Prior Publication Data

US 2005/0107632 A1 May 19, 2005

(51) Int. Cl.$^7$ ............................................ C07C 381/00
(52) U.S. Cl. ........................ 562/824; 562/821; 562/826
(58) Field of Search ................................ 562/824, 821, 562/826

(56) References Cited

U.S. PATENT DOCUMENTS

| | | | |
|---|---|---|---|
| 4,535,011 A | | 8/1985 | Kovacina et al. |
| 5,741,935 A | * | 4/1998 | Bowden et al. ............... 568/74 |
| 6,479,645 B1 | | 11/2002 | Lal et al. |

FOREIGN PATENT DOCUMENTS

| | | | | |
|---|---|---|---|---|
| WO | WO 94/22817 | * | 10/1994 | ......... C07C/381/00 |
| WO | WO 99/2285 | * | 5/1999 | ............ B01J/19/00 |

OTHER PUBLICATIONS

Bowden et al., A New Method for the Synthesis of Aromatic Sulfurpentafluorides and Studies of the Stability of the Sulfurpentafluoride Group in Common Synthetic Transformations, Tetrahedron, 56, 2000, 3399–3408.*
Samai Ayt–Mohand, New and Convenient Method for Incorporation of Penta . . . , Organic Letters, 2002, pp. 3013–3015, vol. 4, 17.
William A. Sheppard, Arylsulfur Pentafluorides, J. Am. Chem. Soc., 1962, pp. 3064–3072, vol. 84.
Roy D. Bowden, A New Method for the Synthesis of Aromatic . . . , Tetrahedron, 2000, pp. 3399–3408, vol. 56.
F.W. Hoover, Synthesis and Chemistry of Ethynylsulfur . . . , J. Am. Chem. Soc., 1964, pp. 3567–3570,.
Peer Kirsch, Liquid Crystals Based on Hypervalent . . . , Angew, Chem. Int. Ed., 1999, pp. 1989–1992, vol. 38.

* cited by examiner

Primary Examiner—Johann Richter
Assistant Examiner—Chukwuma Nwaonicha
(74) Attorney, Agent, or Firm—Geoffrey L. Chase

(57) ABSTRACT

A new route has been found leading to the formation of pentafluorosulfuranyl arylenes. In its broadest aspect the process comprises:

effecting dehydrohalogenation or dehydrogenation of a pentafluorosulfuranyl cycloaliphatic compound represented by either of the structures:

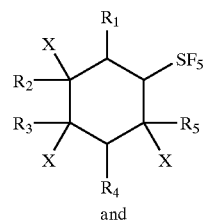

A

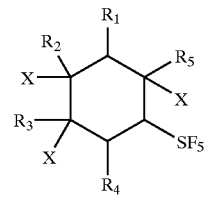

B wherein $R_{1-5}$ are H, halogen, $C_{1-10}$ alkyl, $C_{1-10}$ alkoxy, $C_{1-10}$ thionyl, $C_{1-10}$ alkyl ether, aryl and substituted aryl, thioether, sulfonyl, carboalkoxy, alkylamino, arylamino, alkylphosphoryl, alkylphosphonyl, arylphosphonyl, arylphosphoryl, and mixtures thereof and X is a halogen atom to form the pentafluorosufuranyl arylene represented by the structures:

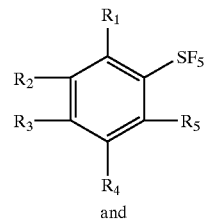

C

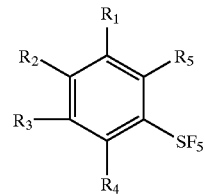

D wherein $R_1$–$R_5$ are as represented above.

18 Claims, No Drawings

SYNTHESIS OF PENTAFLUOROSULFURANYL ARYLENES

BACKGROUND OF THE INVENTION

The development of synthetic methodologies for the introduction of sulfurpentafluoride or pentafluorosulfuranyl groups ("$SF_5$") into organic compounds has been pursued with a considerable degree of interest. The $SF_5$ group imparts unique properties to these organic compounds that include, inter alia, low surface energy, high chemical resistance, high thermal stability, high electronegativity, hydrophobicity, and high dielectric constant. The high electronegativity value of the $SF_5$ group, 3.62 on the Pauling scale, and its greater electron withdrawing ability makes it an attractive alternative for the trifluoromethyl group ("$CF_3$") found in many commercial products. Illustrative of such compositions containing $SF_5$ include pentafluorosulfuranyl fluoroaliphatic compositions, sulfur pentafluorophenyl pyrazoles, and arylsulfur pentafluorides, the latter finding applications in liquid crystals.

The following articles and patents are representative of methods for introducing $SF_5$ groups into organic compounds.

U.S. Pat. No. 4,535,011 discloses a process for producing mono(pentafluorosulfur diacetylene polymers wherein sulfur pentafluoro bromide is first reacted with acetylene at temperatures below about $-70°$ C. and then the resulting intermediate debrominated. Dehydrobromination is effected by reacting the intermediate adduct with a strong base, e.g., potassium hydroxide.

U.S. Pat. No. 6,479,645 discloses methods for producing sulfurpentafluoride compounds having a substituted silyl group. In the disclosed process, sulfur pentafluoro bromide is reacted with a trisubstituted silyl acetylene in the presence of potassium fluoride at room temperature. Bromine is removed from the intermediate compound by addition of powdered potassium hydroxide.

The article, *New and Convenient Method for Incorporation of Pentafluorosulfanyl ($SF_5$) Substituents Into Aliphatic Organic Compounds*, Samai Ayt-Mohand and W. Dolbier, Organic Letters, 2002, 4, 17, 3013 discloses the addition of the $SF_5$-group to organic compounds by the reaction of $SF_5Cl$ with alkynes and alkenes in the presence of triethylborane and hexane solvent at temperatures from $-30°$ C. to room temperature.

Sheppard, et al, W. A. J. Am. Chem. Soc. 1962, 84, 3064., disclose the formation of phenylsulfur pentafluoride and nitrophenylsulfur pentafluoride by reacting aryl disulfides with silver difluoride in ~30% yield.

Bowden, R. D., et al, D. *Tetrahedron*, 2000, 56, 3399, disclose the reaction of aryl disulfides with $F_2$ in the presence of $CH_3CN$. This reaction produces electron-deficient arylsulfur pentafluorides, e.g., ortho and para nitrophenylsulfur pentafluoride.

Hoover, F. W; et al., J. Am. Chem. Soc. 1964, 3567, disclose a procedure for the production of phenylsulfur pentafluoride and dimethylphenylsulfur pentafluoride by the Diels-Alder cycloaddition reaction of butadiene and 2,3-dimethylbutadiene respectively with ethynylsulfur pentafluoride.

BRIEF SUMMARY OF THE INVENTION

In accordance with the invention, a new route has been found leading to the formation of pentafluorosulfuranyl arylenes. In its broadest aspect the process comprises: effecting dehydrohalogenation or dehydrogenation of a pentafluorosulfuranyl cycloaliphatic compound represented by either of the structures:

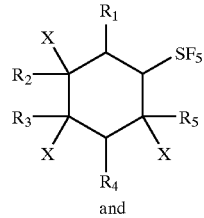

A

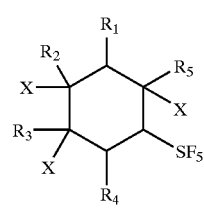

B to form a pentafluorosufuranyl arylene represented by the structures:

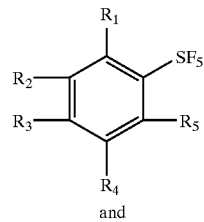

C

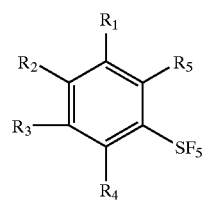

D wherein $R_{1-5}$ are H, halogen, e.g., Cl, or Br; $C_{1-10}$ alkyl, $C_{1-10}$ alkoxy, $C_{1-10}$ thionyl. $C_{1-10}$ alkyl ether, aryl and substituted aryl, thioether, sulfonyl, carboalkoxy, alkylamino, arylamino, alkylphosphoryl, alkylphosphonyl, aryphosphonyl, and arylphosphoryl, etc. X is a halogen, preferably Br, Cl, or mixture thereof. (Although not shown the remaining valences are satisfied by H.) Typically, only one or two of $R_{1-5}$ are other than H. Specific examples of groups other than H include: $CH_3$, $OCH_3$, t-butyl, $(CH_2)_nCl$, $(-CH_2)_nS(CH_2)_mCH_3$, $-SCH_3$, $-N(CH_3)_2$, $-(CH_2)_nN(CH_3)(CH_2)_mCH_3$, $-SO_2CH_3$, $-PO(OEt)_2$, and $P(CH_3)_2$, etc. where n and m are integers, typically from 1–10. In the preferred embodiment, $R_{1-5}$ are H and X is Br.

DETAILED DESCRIPTION OF THE INVENTION

Arylsulfur pentafluorides have found application in liquid crystals and other electro-optical fields. The key to the process reaction leading to the formation of the aryl sulfur pentafluorides is in the ability to employ cyclohexadiene or derivative thereof as a base material. The starting material for the process is represented by the formula:

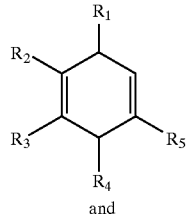

E and

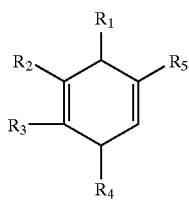

F wherein $R_{1-5}$ are as represented above, i.e., H, halogen, e.g., Cl, or Br; $C_{1-10}$ alkyl, $C_{1-10}$ alkoxy, and $C_{1-10}$ thionyl, $C_{1-10}$ alkyl ether, aryl and substituted aryl, thioether, sulfonyl, carboalkoxy, alkylamino, arylamino, alkylphosphoryl, alkylphosphonyl, aryphosphonyl, and arylphosphoryl, etc. (Although not shown the remaining valences are satisfied by H.). X is a halogen, preferably Br, Cl or mixture thereof. Br is preferred.

There are at least two routes for producing compounds A and B from compounds E and F. A first route (1) involves the reaction of $SF_5X$ where X is Cl or Br, preferably Br, with compounds represented by the structures E or F followed by halogenation, and a second route (2), involves the initial halogenation of compounds represented by the structures E or F to produce compounds represented by the structures G or H:

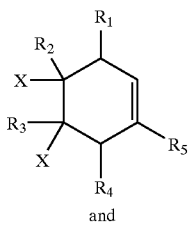

G and

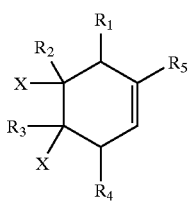

H followed by reaction with $SF_5X$.

To facilitate an understanding of route 1, $SF_5X$, i.e., $SF_5Br$ and $SF_5Cl$, is reacted with cyclohexadiene or a derivative thereof by condensing the $SF_5X$ reactant in the olefins E or F under liquid phase conditions. When X is Br the resulting intermediate compounds are represented by the structures:

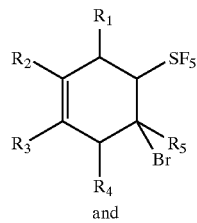

I and

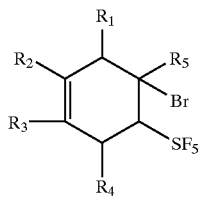

J wherein $R_{1-5}$ are as recited above.

The reaction stoichiometry involving the reaction of $SF_5X$, e.g., $SF_5Br$, with 1,4-cyclohexadiene, or a derivative thereof, is generally consistent with the level of $SF_5$ addition desired. Typically the reaction stoichiometry employs a slight excess of $SF_5X$ reactant, e.g., from 1.05 to 1.2 moles $SF_5X$ per mole of cyclohexadiene.

The reaction preferably is carried out in the presence of a free radical initiator such as a trialkyl borane, e.g., triethyl borane, organic peroxides such as benzoyl peroxide and t-butyl hydroperoxide, azo compounds, azobutyronitrile, and irradiation by ultra violet light etc.

The free radical initiator employed to facilitate the addition of $SF_5$ and X across a double bond in cyclohexadiene, e.g., triethylborane is added in an amount of 1–25 mol %, preferably 5–10 mol %, per mole of the olefin to be treated. Triethyl borane is the preferred initiator in view of its reactivity at low temperatures, e.g., a low as −78° C. Absent the use of a free radical initiator addition of the $SF_5$ group and halogen atom is essentially nil.

The reaction of $SF_5X$, e.g., $SF_5Br$, with the cyclohexadiene or derivative thereof is carried out at temperatures below the decomposition of $SF_5X$, but above the activation temperature for the free radical initiator. The advantage of triethyl borane as a free radical initiator is that it is active at a low temperature, from about −90° C. to the boiling point of solvent or olefin, preferably low temperatures from −80 to +50° C., and most preferably −75° C. to 0° C. Thus, in carrying out step 1 of the process, $SF_5X$ is condensed into the reaction medium and then the reaction carried out under liquid phase conditions. Low temperature reaction also minimizes the formation of polymerization byproducts.

The reaction of $SF_5X$ with cyclohexadiene or derivative can be carried out in a wide range of liquid mediums, i.e., the reaction can be carried out in the presence of olefin neat or it can be carried out in the presence of solvents. Representative solvents suited for carrying out the reaction include hydrocarbons, fluorocarbons, nitriles, ethers, and halocarbons. Solvent levels of from 10 to 100% by weight of the olefin can be used.

The second step in route (1), and the synthesis of compounds represented by the structures A and B, involves the halogenation of compounds represented by the structures I and J generated on reaction of $SF_5X$ with cyclohexadiene or a derivative thereof. Halogenation can be effected in conventional manner by reacting compounds I and J with a halogen, e.g., $Cl_2$, $Br_2$, or $I_2$. Preferably $Br_2$ is used as the halogenating agent. Temperatures for halogenation range from −78° C. to the boiling point of the solvent preferably −20 to 0° C.

Route 2, as described, comprises effecting initial halogenation of the initial cyclohexadiene or its derivative represented by the structures E and F to produce compounds represented by the structures K and L, respectively.

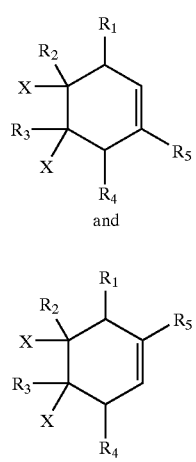

wherein the R and X groups are as recited for compounds represented by the structures G and H. X in the formula can be Br, Cl, I or mixture.

Halogenation is effected using $Cl_2$, $Br_2$, or $I_2$ in the same manner as the halogenation of the pentafluorosulfuranyl cyclohexene derivative in route 1.

The second step in the route 2 procedure, and leading to the formation of the compounds represented by structures A and B, resides in reacting $SF_5X$ with the halogenated cyclohexene or halogenated cyclohexene derivatives compounds represented by the structures K and L. The procedure set forth in route 1 for effecting reaction of $SF_5X$ with cyclohexadiene or derivative may be used here. A free radical initiator should be used where X is halogen, and particularly in the favored reaction, when reacting $SF_5Br$ with the brominated cyclohexadiene or derivative is employed.

Step 3 of the overall procedure involves the dehydrohalogenation or dehydrogenation of the compounds represented by the structures A and B, whether produced by the practice of either route 1 or route 2, as described. An advantage of using $SF_5Br$ to $SF_5Cl$ and using bromine in the formation of compounds represented by the structures A and B is manifested in effecting dehydrohalogenation. The bromine atom facilitates removal from the thus formed product. Removal of HX can be effected by addition of a strong base, e.g., alkali or alkaline earth metal hydroxides, alkoxides, amides, amines, metal alkyl derivatives. Powdered sodium hydroxide is well suited for effecting dehydrohalogenation and is preferred. The rate of addition must be such that the exothermic dehydrohalogenation, e.g., dehydrobromination reaction does not cause the reaction mixture to exceed 30° C. and preferably 25° C. It is possible to carry out the dehydrobromination at a temperature as low as 10° C. Preferably the temperature is from 20 to 25° C. In order to ensure that dehydrobromination is complete, an excess of potassium hydroxide is used. The preferred excess is from 25 to 100 mole percent of stoichiometry. On elimination of three moles of HX, e.g., HBr, pentafluorosulfuranyl arylenes represented by structures C and D are produced.

In an alternative embodiment of step 3, compounds represented by the structures A and B may be converted to compounds C and D respectively by using dehydrogenation metal catalysts such as Pt, Pd, Rh, and Ru and reacting under dehydrogenation conditions. Dehydrogenation can be carried out in conventional manner.

Products from the process can be purified by standard methods including distillation and chromatography.

The following representative three step process to pentafluorosulfuranyl arylenes is described in the following reaction sequence and illustrated specially in the examples. The examples are intended to illustrate various embodiments of the invention and are not intended to restrict the scope thereof.

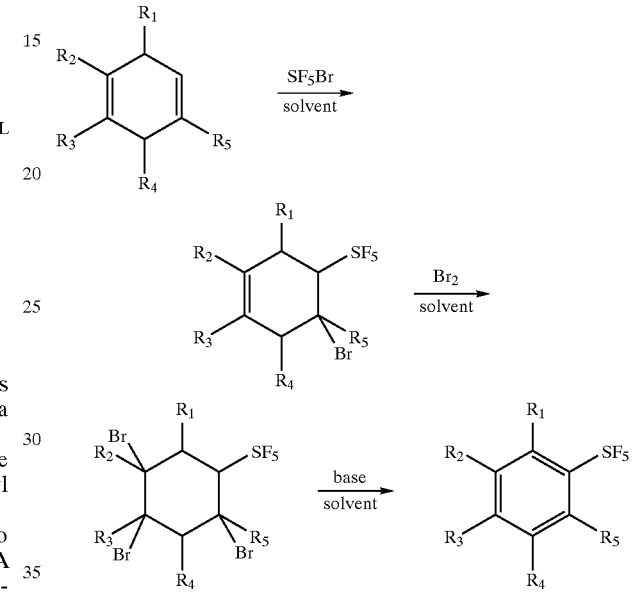

EXAMPLE 1

$SF_5Br$ Addition to Cyclohexadiene at −78° C.

1,4 Cyclohexadiene (75 mmole), pentane (300 mL), potassium fluoride (12 mmole) and triethylborane (7 mmole, 1 M in hexanes) were charged to a Teflon lined ss Parr reactor. The solution was cooled to −45° C. and degassed. $SF_5Br$ (75 mmole) was then slowly condensed into solution while stirring. The temperature was maintained at −45° C. for one hour then the solution was allowed to warm to room temperature. After one hour the reactor was vented and purged with $N_2$. The reaction mixture was slowly added to a cold sodium bicarbonate solution. The product was isolated from the organic layer in 90% yield and analyzed by GC, GC/MS and NMR. The results are as follows: MW=287, GC/MS m/z 288, 286, 207, 262, 159, 127, 99, 89, 79, 77, 51, $^1$H NMR δ=2.6 (d, 1H), 3.0 (dt, 3H), 4.5 (q, 1H), 5.0 (d, 1H), 5.8 (m, 2H), and $^{19}$F NMR δ=55 (d, 4F), 84 (p, 1F).

EXAMPLE 2

Bromination of Pentafluorosulfuranyl Cyclohexene

The product of Example 1 was mixed with methylene chloride (100 mL) and cooled to −30° C. Bromine (75 mmol) diluted in methylene chloride (50 mL) was added drop-wise to the flask and stirred for 3 hours. The solution was then treated with saturated sodium bicarbonate solution and rinsed with water. The product was isolated from the methylene chloride in 92% yield and analyzed by GC, GC/MS and NMR. The results are as follows: MW=447, GC/MS m/z 448, 447, 446, 445, 368, 367, 366, 287, 285, 238, 237, 236, 205, 179, 177, 127, 97, 79, 77, 51, $^1$H NMR δ=2.7(m, 1H), 3(s, 2H), 3.1(s, 1H), 4.4(s, 2H), 4.5(m, 1H), 4.8(s, 1H), and $^{19}$F NMR δ=58(4F, d), 83(p,1F)

EXAMPLE 3

Dehydrobromination of Brominated Pentafluorosulfuranyl Cyclohexene

The product of Example 2 was stirred overnight with tetrahydrofuran (100 mL) and six molar equivalents of powdered sodium hydroxide (450 mmol). The base was removed by filtering and solvent was removed by distillation at atmospheric pressure. The product was purified by distillation at 24° C., 1 Torr and analyzed by GC, GC/MS and NMR. Yield was 72%. The results are as follows: MW=204, GC/MS m/z 204, 185, 127, 96, 77, 51, $^1$H NMR δ=7.4–7.5 (m, 3H), 7.7(d, 2H) and $^{19}$F NMR δ=62 (d, 4F), 84(p, 1F).

What is claimed is:
1. A process for making pentafluorosulfuranyl arylenes which comprises:

effecting dehydrohalogenation or dehydrogenation of a halogenated pentafluorosulfuranyl cycloaliphatic compound represented by either of the structures:

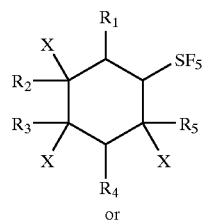

A or

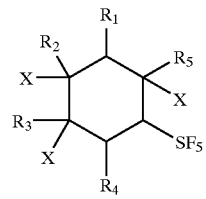

B to form pentafluorosulfuranyl arylene compounds represented by either of the structures:

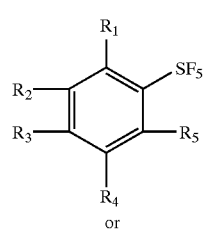

C or

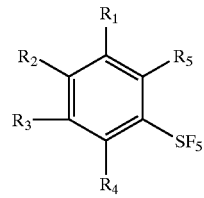

D wherein $R_{1-5}$ are H, halogen, $C_{1-10}$ alkyl, alkoxy, $C_{1-10}$ thionyl, $C_{1-10}$ alky ether, aryl and substituted aryl, thioether, sulfonyl, carboalkoxy, alkylamino, arylamino, alkylphosphoryl, alkylphosphonyl, arylphosphonyl, arylphosphoryl and mixtures thereof and X is a halogen atom.

2. The process of claim 1 wherein $R_{1-5}$ are H.
3. The process of claim 2 wherein X is selected from the group consisting of Br and Cl or a mixture thereof.
4. The process of claim 3 wherein compounds C and D are formed by effecting dehydrohalogenation at compounds represented by the structures A or B.
5. The process of claim 4 wherein X is bromine.
6. The process of claim 5 wherein dehydrohalogenation is effected by reaction of compounds represented by the structures A and B with powdered sodium hydroxide.
7. The process of claim 1 wherein the halogenated pentafluorosulfuranyl cycloaliphatic compounds for forming the pentafluorosulfuranyl arylenes are formed by a two step process which comprises:

(a) reacting SF$_5$X with a compound represented by either of the structures:

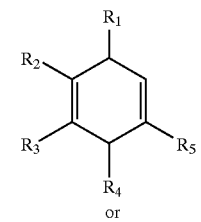

E or

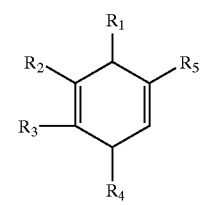

F leading to the formation of compounds represented by either of the structures:

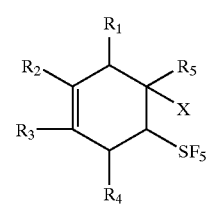

I

-continued

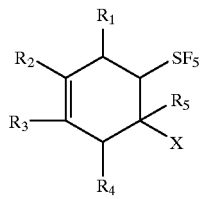

J wherein $R_{1-5}$ are H, halogen, $C_{1-10}$ alkyl, $C_{1-10}$ alkoxy, $C_{1-10}$ thionyl, $C_{1-10}$ alkyl ether, aryl and substituted aryl, thioether, sulfonyl, carboalkoxy, alkylamino, arylamino, alkylphosphoryl, alkylphosphonyl, arylphosphonyl, arylphosphoryl and mixtures thereof and X is Br or Cl;

and then, (b) halogenating the thus formed compounds represented by the structures I and J produced in step (a) by reaction with $Cl_2$, $B_2$, or $I_2$ to form the halogenated pentafluorosulfuranyl cycloaliphatic compounds represented by the structures A and B.

8. The process of claim 7 wherein $R_{1-5}$ are H.

9. The process of claim 8 wherein step (a) is carried out using $SF_5Br$ as the reactant.

10. The process of claim 9 wherein a free radical initiator is used to catalyze the reaction of $SF_5Br$ with compound represented by the structures E or F.

11. The process of claim 10 wherein the free radical initiator is triethyl borane.

12. The process of claim 11 wherein halogenation in step (b) is carried out using $Br_2$ as the halogenating agent.

13. The process of claim 12 wherein compounds represented by the structures C and D are formed by effecting dehydrohalogenation of compounds represented by the structures A and B by reaction with powdered sodium hydroxide.

14. The process of claim 1 wherein the halogenated pentafluorosulfuranyl cycloaliphatic compounds for forming the pentafluorosulfuranyl arylenes are formed by a two step process which comprises:

(a) halogenating a compound represented by the structures:

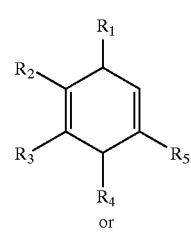

E or

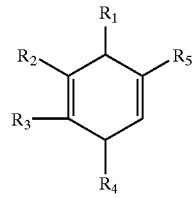

F leading to the formation of compounds represented by the structures:

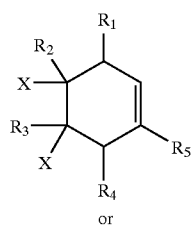

K or

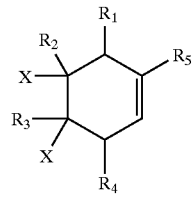

L wherein $R_{1-5}$ are H, halogen; $C_{1-10}$ alkyl, $C_{1-10}$ alkoxy, $C_{1-10}$ thionyl, $C_{1-10}$ alkyl ether, aryl and substituted aryl, thioether, sulfonyl, carboalkoxy, alkylamino, arylamino, alkylphosphoryl, alkylphosphonyl, arylphosphonyl, arylphosphoryl and mixtures thereof and X is Br or Cl;

and then, (b) reacting the thus formed compounds K and L produced in step (a) by reaction with $SF_5X$ to produce compounds represented by the structures A or B.

15. The process of claim 14 wherein $R_{1-5}$ are H and X is Br.

16. The process of claim 15 wherein step (a) is carried out using $SF_5Br$ as the reactant and a free radical initiator is used to catalyze the reaction of $SF_5Br$ with the compounds represented by the structures K or L.

17. The process of claim 16 wherein the free radical initiator is triethyl borane.

18. The process of claim 16 wherein C and D are formed by effecting dehydrohalogenation of compounds represented by the structures K and L by reaction with powdered sodium hydroxide.

* * * * *